United States Patent [19]

Fosslien

[11] Patent Number: 4,527,438
[45] Date of Patent: Jul. 9, 1985

[54] AUTOMATIC FEED SYSTEM FOR SAMPLING APPARATUS

[75] Inventor: Egil Fosslien, Glenview, Ill.

[73] Assignee: Cortex Research Corporation, Northbrook, Ill.

[21] Appl. No.: 536,715

[22] Filed: Sep. 28, 1983

[51] Int. Cl.³ ............................................. G01N 35/04
[52] U.S. Cl. .............................. 73/864.81; 73/864.24; 198/339; 198/625
[58] Field of Search ........... 73/864.21, 864.23, 864.81; 422/63, 64, 65, 67; 198/339, 472, 625

[56] References Cited

U.S. PATENT DOCUMENTS

| | | | |
|---|---|---|---|
| 3,902,372 | 9/1975 | MacKinnon | 73/864.85 |
| 4,120,662 | 10/1978 | Fosslien | 73/425.6 |
| 4,311,484 | 1/1982 | Fosslien | 73/864.21 |
| 4,454,095 | 6/1984 | Holt | 422/64 |

Primary Examiner—S. Clement Swisher
Attorney, Agent, or Firm—Senniger, Powers, Leavitt and Roedel

[57] ABSTRACT

An automatic feed system for use with blood sampling apparatus of the type comprising a first conveyor for conveying a series of stoppered tubes to a sampling station and for imparting a motion to the tubes to mix the contents of the tubes as they are conveyed to the sampling station, and a needle for penetrating each tube when it arrives at the sampling station to withdraw a specimen sample therefrom. The feed system comprises a second conveyor for conveying a series of such tubes one after another to a pick-up station, and a tube-transfer device for transferring a tube at the pick-up station from the second conveyor to the first conveyor of the sampling apparatus for conveyance to the sampling station.

18 Claims, 6 Drawing Figures

AUTOMATIC FEED SYSTEM FOR SAMPLING APPARATUS

BACKGROUND OF THE INVENTION

This invention relates to sampling apparatus of the type disclosed in my co-assigned U.S. Pat. No. 4,120,662 and 4,311,484 and, more particularly, to an automatic feed system for such apparatus.

In the sampling apparatus described in U.S. Pat. No. 4,120,662, stoppered tubes containing specimens of the fluid (e.g., blood) to be sampled have to be loaded by hand into the apparatus. It is necessary to interrupt operation of the machine during such loading, which reduces the efficiency of the sampling process.

The sampling apparatus described in U.S. Pat. No. 4,311,484 incorporates a continuous feed system. However, while this system has proven to be generally satisfactory, it has certain drawbacks. Thus in the feed system described in the 484 patent, tubes loaded into the system are stacked one atop another, which may lead to jamming of the machine if adjacent tubes or the adhesive labels thereon happen to stick to one another. Also, in this prior system the tubes are virtually inaccessible once they are loaded into the machine.

SUMMARY OF THE INVENTION

Among the several objects of this invention may be noted the provision of an improved feed system for sampling apparatus of the type described in my above-mentioned co-assigned U.S. patents; the provision of such apparatus which is adapted for maintaining the containers (e.g., stoppered tubes) physically separate from one another to minimize the possibility of jamming; the provision of such a system wherein containers may be loaded into the system without interrupting operation of the machine; the provision of such a feed system wherein the containers in the system are individually accessible even after loading; and the provision of such a system which is reliable in operation.

Generally, a feed system of the present invention is adapted for use with apparatus for obtaining samples from specimens of blood or the like contained in closed containers, such as stoppered tubes, said apparatus being of the type comprising first conveyor means for conveying a series of said tubes to a sampling station and for imparting a motion to the tubes to mix the contents of the tubes as they are conveyed to said sampling station, and means for penetrating each tube when it arrives at the sampling station to withdraw a specimen sample therefrom. The feed system comprises second conveyor means for conveying a series of said tubes one after another to a pick-up station, and tube-transfer means for transferring a tube at said pick-up station from the aforesaid second conveyor means to said first conveyor means for conveyance to the sampling station.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 2:
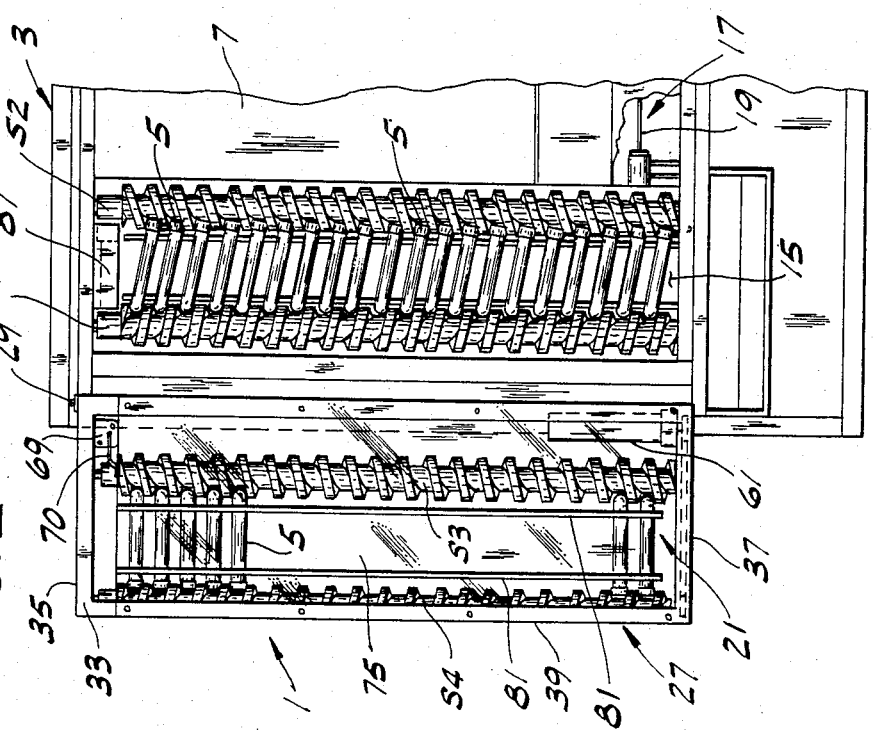
FIG. 2 is a view similar to FIG. 1 showing a housing for the feed system swung open to allow access to the sampling apparatus.

Referring now to the drawings, first more particularly to FIGS. 1 and 2, there is generally indicated at 1 an automatic feed system for sampling apparatus, generally designated 3, which, except as noted below, is essentially of the same construction as the sampler shown in my aforesaid U.S. Pat. No. 4,311,484, the disclosure of which is hereby incorporated herein by reference. As described in detail in that patent, sampling apparatus 3 is operable to obtain samples from specimens of blood, for example, from closed containers, such as stoppered test tubes 5, and to deliver such samples to an analyzer (not shown) for analysis.

As illustrated best in FIG. 2, sampling apparatus 3 comprises a cabinet having a front 7, back (not shown) and two opposing sides 11. A pair of substantially parallel vertical screw shafts S1 and S2 are mounted within the cabinet toward the front of the cabinet for rotation about axes lying in a vertical plane extending generally in side-to-side direction with respect to the cabinet. Each of these shafts S1, S2 is screw-threaded to have spiral flights 13 along substantially the entire lengths of the shafts, the top flight of each shaft being spaced below the top of the shaft by a distance somewhat greater than the diameter of the tubes to be handled. As described in detail in U.S. Pat. No. 4,311,484, screw shafts S1 and S2 are rotatable in opposite directions by a motor (not shown) and constitute first conveyor means for conveying a series of stoppered tubes downwardly to a sampling station 15, and for imparting a gentle rocking and rotating motion to the tubes as they are being so conveyed to mix the contents of the tubes. Screw shafts S1 and S2, hereinafter referred to as mixing screws, are spaced apart for holding tubes 5 generally horizontally with the ends of the tubes supported by respective flights of the screws. The distance between mixing screws S1 and S2 is suitably adjustable (e.g., see my U.S. Pat. No. 4,120,662) for accommodating tubes of different lengths.

Sampling apparatus 3 is equipped with an aspiration and transfer system 17 (not shown in its entirety) of the type described in U.S. Pat. No. 4,311,484 for aspirating a specimen sample from each tube 5 when it reaches sampling station 15 and for then delivering the sample to the intake line of an analyzer. This aspiration system includes means constituted by an elongate horizontally disposed needle 19 having a longitudinal passage therethrough for penetrating the stoppered (right) end of a tube at the sampling station to withdraw a specimen sample therefrom. Reference should be made to U.S. Pat. No. 4,311,484 for a detailed description of the construction and operation of this aspiration system.

The automatic feed system 1 of the present invention generally comprises a second conveyor means, generally designated 21 for conveying a series of specimen-filled tubes 5 one after another to a pick-up station 23 and tube-transfer means, generally designated 25, for transferring a tube at the pick-up station to the mixing screws S1, S2 for conveyance to the sampling station 15.

More specifically, conveyor means 21 comprises a second pair of vertical screw shafts S3, S4 (hereinafter referred to as feed screws) mounted within a housing, generally designated 27, hinged at 29 on the front of the cabinet for swinging on a generally vertical axis between open (FIG. 2) and closed (FIG. 1) positions. The housing 27 is generally rectangular in shape, having front, back, top, bottom, and side walls indicated at 31, 33, 35, 37 and 39, respectively. Feed screws S3 and S4 are mounted within the housing for rotation on axes lying in a generally vertical plane which extends generally in side-to-side direction with respect to the housing, the arrangement being such that when the housing is closed the feed screws S3, S4 are positioned immediately forward of and in generally front-to-back alignment with the mixing screw S1, S2 (see FIG. 3). The feed screw S3, S4 are essentially identical in construction to the mixing screws S1, S2, having spiral flights indicated at 41 for supporting a series of tubes in generally horizontal position with the ends of the tubes resting on respective flights of the feed screws. The feed screws are rotatable in opposite directions to convey tubes 5 upwardly with each tube finally reaching pick-up station 23 wherein it spans the top flights 41 of the two feed screws (see FIG. 4) for pick-up by transfer means 25.

Figure 6:
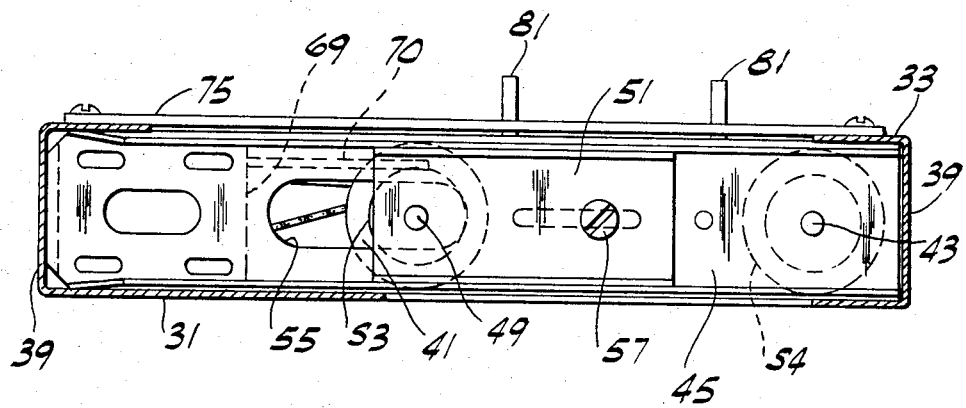
FIG. 6 is an enlarged horizontal section taken on line 6—6 of FIG. 1.

As shown best in FIGS. 4 and 6, the spindle ends 43 of feed screw S4 are journalled in upper and lower channel-shaped brackets designated 45 and 47, respectively, the former being secured in fixed position to the housing 27 immediately below the top wall 35 of the housing and the latter being secured in fixed position to the housing immediately above the bottom wall 37 of the housing. The spindle ends 49 of feed screw S3 are journalled in a second pair of channel brackets designated 51 and 53 slidable in brackets 45 and 47, respectively, for adjustment of feed screw S3 toward and away from feed screw S4 for accommodating tubes of any length within the range of adjustment. The fixed upper and lower brackets 45, 47 are slotted as indicated at 55 to enable such adjustment. Feed screw S3 is secured in adjusted position by tightening a pair of screws, one of which is indicated at 57 in FIG. 6.

Figure 3:
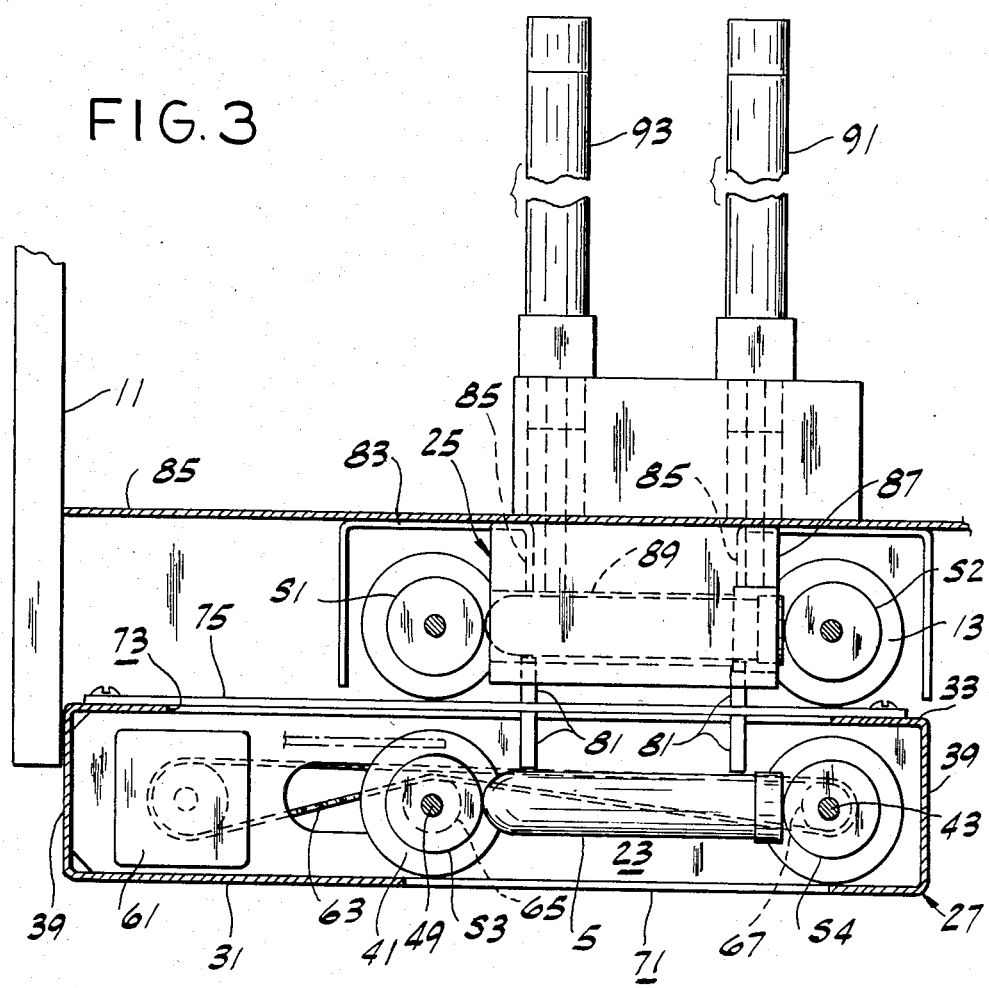
FIG. 3 is an enlarged horizontal section on line 3—3 of FIG. 1.

Feed screws S3 and S4 are rotated in opposite directions by a motor 61 bracket-mounted in the housing 27 driving a chain 63 trained around respective sprockets 65 and 67 on the lower spindle ends 43, 49 of the screws, as shown in FIG. 3. The operation of the motor is controlled by a switch 69 mounted on upper bracket 45 adjacent the top wall 35 of the housing. The switch has means indicated at 70 for sensing the rotary position of feed screw S3.

Figure 1:
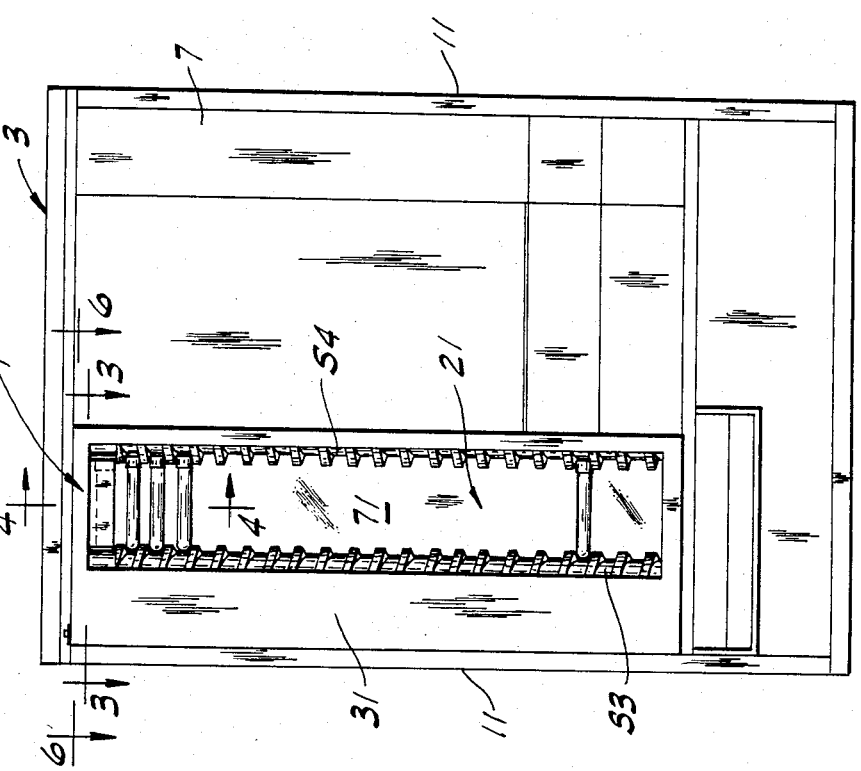
FIG. 1 is a front elevation of sampling apparatus equipped with a feed system of the present invention.

The front wall 31 of the housing 27 has a relatively large rectangular opening 71 therein providing access to feed screws S3 and S4 for loading them with tubes from the front of the housing when the latter is closed as shown in FIG. 1. The back wall 33 of the housing also has a large opening 73 therein exposing the feed screws S3, S4 to view when the housing is swung open to the position shown in FIG. 2. This latter opening is substantially closed by plate means constituted by a panel 75 of generally transparent material such as acrylic plastic fastened to the back wall of the housing. The upper edge of panel 75 is spaced below the top of the opening 73 in the back wall of the housing, leaving a gap or passageway 77 through which a tube 5 at pick-up station 23 is accessible from the back of the housing 27 by transfer means 25. Panel 75 has a pair of vertical retaining members or bars 81 on each of its front and back faces lying in planes extending in front-to-back direction with respect to the housing 27 (see FIG. 3). The forward edges of the retaining bars 81 on the front of the panel are engageable by tubes 5 carried by feed the screws S3, S4 (the flights 41 of which are inclined downwaroly toward the retaining bars) to maintain the tubes properly positioned in front-to-back direction on the flights 41 of the screws. When the housing is closed, the retaining bars 81 on the back face of the panel 75 cooperate with a pair of elongate retaining members 83 secured in vertical position on a mounting plate 85 rearward of the mixing screws S1, S2 for maintaining the tubes carried by the latter two screws in proper position on the flights 13 of those screws. Retaining members 83 are generally J-shaped in cross section and have parallel opposing flanges 85 projecting forwardly from mounting plate 85 for engagement by tubes 5 carried by the mixing screws S1, S2, the flights of which are inclined downwardly toward the flanges 85.

Transfer means 25 comprises a shuttle member or block 87 having a downwardly-opening recess 89 therein sized and shaped to accommodate a single stoppered tube 5. The shuttle member is mounted on the piston ends of two pneumatic cylinders 91, 93 (constituting cylinder means) suitably affixed to mounting plate 85. These cylinders may be Model 013-D air cylinders sold by Bimba Manufacturing Company of Monee, Ill. The cylinders are extensible and retractible in unison for moving the shuttle member 87 generally horizontally through the passageway 77 in the back of the housing 27 between a first position (FIG. 4) in which the shuttle member is disposed at the tube pick-up station 23 between the upper ends of the feed screws S3, S4 and positioned for the upward entry into recess 89 of a tube conveyed upwardly by the feed screws, and a second position (FIG. 5) in which the shuttle member is disposed between the upper ends of the mixing screws S1, S2 immediately above the upper flights 13 of those shafts for the deposit thereon of a tube within recess 89 for conveyance of the tube down to the sampling station 15. As the shuttle member 87 moves from its first (tube pick-up) position to its second (tube-deposit) position, the tube in recess 89 is supported by the top edges of retaining bars 81 which bridge the top flights 13, 41 of the mixing and feed screws.

The shuttle cylinders 91, 93 are preferably operable in response to movement of the aspirating needle 19 between its extended (tube-penetrating) and retracted (non-penetrating) positions. Thus, in the preferred embodiment of this invention, the shuttle cylinders are extensible to move the shuttle member 87 from its tube-deposit position to its tube pick-up position when the needle moves to its extended position for penetrating a stoppered tube at the sampling station 15 to withdraw a sample therefrom (at which time the mixing screws S1, S2 are not rotating), and retractable to move the shuttle member from its tube pick-up position back to its tube-deposit position when the needle retracts from the tube (at which time the mixing screws resume rotation to deliver another tube to the sampling station 15). It will be understood that the circuitry described in U.S. Pat.

No. 4,311,484 may be modified in a manner familiar to those skilled in this field for accomplishing these results.

To operate the sampling apparatus 3 and automatic feed system 1 of the present invention, tubes 5 from which specimen samples are to be withdrawn for analysis are loaded between respective flights 13 of the mixing screws S1, S2 and the housing 27 swung shut to the position shown in FIG. 1. Additional tubes 5 are then loaded between the flights 41 of the feed screws S3, S4 and the appropriate control button actuated to start the machine. On start-up, the sampling apparatus 3 will operate in essentially the same manner described in the aforesaid U.S. Pat. No. 4,311,484, and reference should be made to that patent for a detailed description of such operation.

Figure 4:
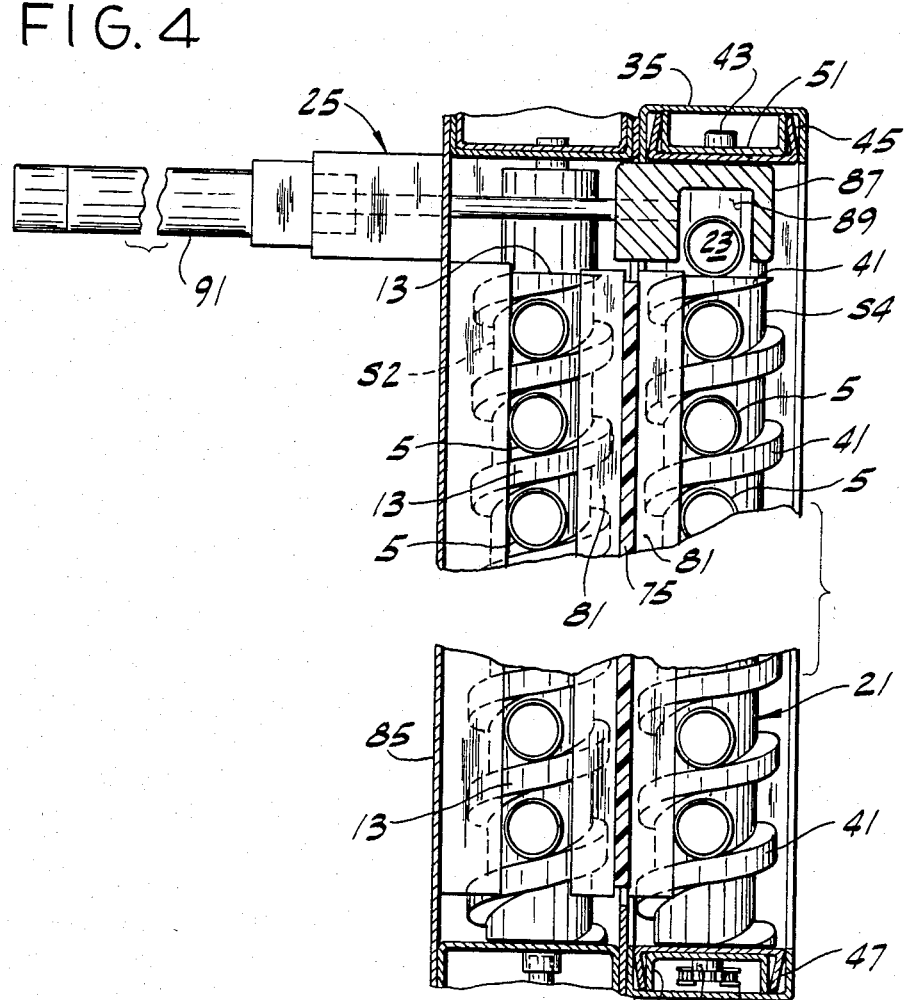
FIG. 4 is an enlarged vertical section on line 4—4 of FIG. 1 showing a shuttle member in a tube pick-up position.
Figure 5:
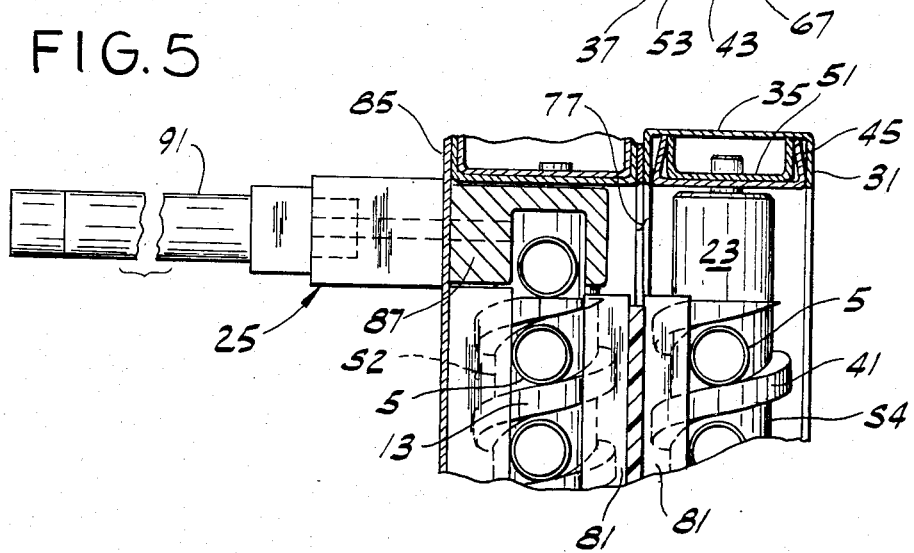
FIG. 5 is a portion of FIG. 4 showing the shuttle member in a tube-deposit position.

Upon movement of the aspiration needle 19 from its retracted to its tube-penetrating position, the shuttle cylinders 91, 93 are operable to move the shuttle member 87 from the tube-deposit position shown in FIG. 4 to the tube pick-up position shown in FIG. 5, whereupon motor 61 is energized to rotate the feed screws S3, S4 to convey a tube up into the recess 89 in the shuttle member. After the feed screws S3, S4 have completed one revolution, as sensed by the sensing means 70 on switch 69, switch 69 is adapted to deenergize the motor 61 to stop further rotation of the feed screws S3, S4. The shuttle cylinders 91, 93 are operable to move the shuttle member 87 to its tube-deposit position upon retraction of the aspirating needle 19 from the tube at the sampling station.

As the shuttle member 87 moves to its stated tube-deposit position, it slides the tube in recess 89 off the top flights 41 of feed screws S3, S4 and across the top edges of the retaining bars 81 to a position above the top flights 13 of the mixing screws S1, S2, whereupon the tube is deposited on such flights. As described in detail in U.S. Pat. No. 4,311,484, mixing screws S1 and S2 begin rotation shortly after the aspirating needle 19 is withdrawn from the tube at the sampling station to convey the next tube to the sampling station 15. Thus the mixing screws S1, S2 may be rotating when the shuttle member 87 carrying a tube arrives at the tube-deposit position. However, it will be understood, that the mixing screws S1, S2 may be held stationary until the shuttle member has deposited a tube thereon.

The above cycle of operation is repeated continuously with tubes 5 being moved incrementally upwardly by feed screws S3 and S4 to pick-up station 23, then horizontally rearwardly by the shuttle member 87 from the pick-up station to the mixing screws S1, S2, and finally incrementally downwardly by mixing screws S1, and S2 to be sampling station 15.

The automatic feed system of this invention is advantageous in that the tubes 5 being conveyed are held spaced apart and out of contact with one another so that adjacent tubes cannot stick together. Moreover tubes can be loaded into the feed system without interrupting the operation of the sampling apparatus. Also, the mixing screws S1, S2 and the tubes carried thereby are readily accessible simply by swinging the housing 27 open to the position shown in FIG. 2.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for obtaining samples from specimens of blood or the like contained in closed containers, such as stoppered tubes, said apparatus comprising first conveyor means for conveying a series of said tubes to a sampling station and for imparting a motion to the tubes to mix the contents of the tubes as they are conveyed to said sampling station, and means for penetrating each tube when it arrives at the sampling station to withdraw a specimen sample therefrom, the improvement comprising a feed system for automatically feeding tubes to said first conveyor means, said feed system comprising second conveyor means for conveying a series of said tubes one after another to a pick-up station, and tube transfer means for transferring a tube at said pick-up station from said second conveyor means to said first conveyor means for conveyance to said sampling station, said tube transfer means comprises a shuttle member movable from a first position for receiving a tube conveyed to the pick-up station by said second conveyor means to a second position for loading by tube onto said first conveyor means.

2. Apparatus as set forth in claim 1 wherein said second conveyor means comprises a pair of generally parallel flight conveyors each having a series of flights spaced at interval therealong, said flights being engageable with the ends of said tubes for conveying them separately in generally parallel spaced-apart relation whereby the tubes are conveyed out of contact with one another.

3. Apparatus as set forth in claim 2 wherein said first and second conveyor means are adapted for conveying tubes in a generally vertical direction and said transfer means is adapted for moving tubes generally horizontally.

4. Apparatus as set forth in claim 3 wherein said second conveyor means is adapted for holding said tubes in a generally horizontal position as the tubes are conveyed generally vertically.

5. Apparatus for obtaining samples from specimens of blood or the like contained in closed containers, such as stoppered tubes, said apparatus comprising first conveyor means for conveying a series of said tubes to a sampling station and for imparting a motion to the tubes to mix the contents of the tubes as they are conveyed to said sampling station, and means for penetrating each tube when it arrives at the sampling station to withdraw a specimen sample therefrom, the improvement comprising a feed system for automatically feeding tubes to said first conveyor means, said feed system comprising second conveyor means for conveying a series of said tubes one after another to a pick-up station, and tube transfer means for transferring a tube at said pick-up station from said second conveyor means to said first conveyor means for conveyance to said sampling station, said second conveyor means being adapted for conveying said tubes upwardly and in generally horizontal position with the tubes being spaced from one another and out of contact with one another, said transfer means being adapted for moving said tubes generally horizontally, and said first conveyor means being adapted for conveying said tubes downwardly.

6. Apparatus as set forth in claim 5 wherein said first conveyor means comprises a first pair of screw shafts rotatable about generally parallel vertical axes lying in a first vertical plane, and said second conveyor means comprises a second pair of screw shafts rotatable about generally parallel vertical axes lying in a second vertical plane generally parallel to and spaced from said first plane, the two screw shafts of each pair having spiral flights thereon and being spaced apart for holding a series of tubes generally horizontally with the ends of the tubes supported by respective flights of the screw shafts.

7. Apparatus as set forth in claim 6 further comprising means for rotating said second pair of screw shafts on their respective axes for conveying a tube upwardly to said pick-up station wherein the tube spans the top flights of said screw shafts, said first pair of screw shafts being rotatable on their respective-axes for conveying tubes downwardly to said sampling station.

8. Apparatus as set forth in claim 6 wherein said transfer means comprises a shuttle member movable between a first position in which it is disposed for receiving a tube conveyed to the pick-up station by said second pair of screw shafts, and a second position in which it is disposed above the upper flights of said first pair of screw shafts for depositing said tube thereon.

9. Apparatus as set forth in claim 8 further comprising means bridging the upper flights of the first and second pairs of screw shafts, said shuttle member being adapted for moving a tube off the upper flights of the second pair of screw shafts and across said bridging means for deposit of the tube onto the upper flights of the first pair of screw shafts.

10. Apparatus as set forth in claim 9 wherein said shuttle member has a downwardly-opening recess therein for receiving a tube conveyed upwardly by said second pair of screw shafts to said pick-up station, said tube being adapted to be deposited on said first pair of screw shafts when the shuttle member moves from said first to said second position.

11. Apparatus as set forth in claim 9 further comprising extensible and retractible cylinder means for moving said shuttle member between said first and second positions.

12. Apparatus as set forth in claim 6 wherein said first pair of screw shafts is housed in a cabinet having a front, back and opposing sides with the screw shafts lying in a plane extending generally side-to-side with respect to the cabinet, said second pair of screw shafts being housed in a housing hinged at the front of the cabinet for swinging about a generally vertical axis between an open position in which the housing is swung away from the front of the cabinet to provide frontal access to the first pair of screw shafts, and a closed position in which the second pair of screws shafts is positioned immediately forward of th first pair of screw shafts.

13. Apparatus as set forth in claim 12 wherein said housing has a front, back and opposite sides with the second pair of screw shafts being disposed within the housing in a generally vertical plane extending side-to-side with respect to the housing, the front of the housing having an opening therein for enabling tubes to be loaded between respective flights of the second pair of screw shafts.

14. Apparatus as set forth in claim 13 further comprising retaining means at the back of the housing engageable by tubes carried by said second pair of screw shafts for maintaining the tubes positioned in front-to-back direction between the shafts.

15. Apparatus as set forth in claim 14 wherein said retaining means comprises plate means extending in side-to-side direction with respect to the housing, and a pair of vertical retaining members on the front face of said plate means.

16. Apparatus as set forth in claim 15 wherein said plate means has a second pair of vertical retaining members on its back face, said second pair of retaining members being adapted, where the housing is closed, to assist in maintaining tubes carried by said first pair of screw shafts in proper position with respect to said shafts.

17. Apparatus for obtaining samples from specimens of blood or the like contained in closed containers, such as stoppered tubes, said apparatus comprising first conveyor means for conveying a series of said tubes to a sampling station and for imparting a motion to the tubes to mix the contents of the tubes as they are conveyed to said sampling station, and means for penetrating each tube when it arrives at the sampling station to withdraw a specimen sample therefrom, the improvement comprising a feed system for automatically feeding tubes to said first conveyor means, and feed system comprising second conveyor means for conveying a series of said tubes one after another to a pick-up station, and tube transfer means for transferring a tube at said pick-up station from said second conveyor means to said first conveyor means for conveyance to said sampling station, said second conveyor means comprising a pair of generally parallel flight conveyors each having a series of flights spaced at intervals therealong, said flights being engageable with the ends of said tubes for conveying them separately in generally parallel spaced-apart relation whereby the tubes are conveyed out of contact with one another.

18. Apparatus as set forth in claim 17 wherein said flight conveyors comprise a pair of generally parallel screw shafts having spiral flights thereon for holding a series of tubes with the ends of the tubes supported by respective flights of the screw shafts.

* * * * *